(12) United States Patent
Cichocki et al.

(10) Patent No.: US 11,717,598 B2
(45) Date of Patent: Aug. 8, 2023

(54) OPERATING ROOM COATING APPLICATOR AND METHOD

(71) Applicant: Ethicon, Inc., Somerville, NJ (US)

(72) Inventors: Frank Richard Cichocki, Easton, PA (US); Duan Li Ou, Warren, NJ (US)

(73) Assignee: Ethicon, Inc., Raritan, NJ (US)

( * ) Notice: Subject to any disclaimer, the term of this patent is extended or adjusted under 35 U.S.C. 154(b) by 147 days.

(21) Appl. No.: 16/697,225

(22) Filed: Nov. 27, 2019

(65) Prior Publication Data

US 2020/0171209 A1 Jun. 4, 2020

Related U.S. Application Data

(60) Provisional application No. 62/773,102, filed on Nov. 29, 2018.

(51) Int. Cl.
*B05B 7/16* (2006.01)
*A61L 27/54* (2006.01)
(Continued)

(52) U.S. Cl.
CPC .......... *A61L 27/54* (2013.01); *A61L 2/03* (2013.01); *A61L 2/07* (2013.01); *A61L 2/20* (2013.01); *A61L 2/26* (2013.01); *A61L 17/005* (2013.01); *A61L 17/145* (2013.01); *A61L 31/10* (2013.01); *A61L 31/14* (2013.01); *A61L 31/16* (2013.01); *B05B 7/1606* (2013.01); *B05B 7/1686* (2013.01); *B05B 12/081* (2013.01); *B05B 15/00* (2013.01); *B05B 17/0615* (2013.01); *B05D 1/02* (2013.01); *B05D 3/0493* (2013.01); *C09D 5/14* (2013.01); *C09D 7/20* (2018.01); *C09D 7/62* (2018.01); *C09D 183/04* (2013.01); *C10M 107/50* (2013.01); *A61L 2202/181* (2013.01); *A61L 2202/182* (2013.01); *A61L 2300/202* (2013.01); *A61L 2300/404* (2013.01); *A61L 2300/606* (2013.01); *A61L 2400/10* (2013.01); (Continued)

(58) Field of Classification Search
CPC .................................................. B05B 7/1686
See application file for complete search history.

(56) References Cited

U.S. PATENT DOCUMENTS

| 3,976,049 A | 8/1976 | Yamashita |
| 4,057,047 A | 11/1977 | Gossett |

(Continued)

FOREIGN PATENT DOCUMENTS

| CN | 1827178 A | 9/2006 |
| CN | 101553359 A | 10/2009 |

(Continued)

OTHER PUBLICATIONS

International Search Report dated Feb. 27, 2020 for Application No. PCT/IB2019/060229.

(Continued)

*Primary Examiner* — Cachet I Proctor (57) ABSTRACT

The present disclosure provides a coating apparatus and method for applying a coating of a therapeutic agent, comprising an openable and sealable device compartment, a therapeutic agent positioned in communication with the device compartment, a thermal source for vaporizing the therapeutic agent, and a vacuum source in fluid communication with the device compartment.

14 Claims, 10 Drawing Sheets

(51) Int. Cl.

| | |
|---|---|
| *A61L 2/03* | (2006.01) |
| *A61L 2/07* | (2006.01) |
| *A61L 2/20* | (2006.01) |
| *A61L 2/26* | (2006.01) |
| *A61L 17/00* | (2006.01) |
| *B05B 15/00* | (2018.01) |
| *A61L 17/14* | (2006.01) |
| *C09D 7/20* | (2018.01) |
| *C09D 7/62* | (2018.01) |
| *A61L 31/10* | (2006.01) |
| *A61L 31/14* | (2006.01) |
| *A61L 31/16* | (2006.01) |
| *C09D 5/14* | (2006.01) |
| *C09D 183/04* | (2006.01) |
| *C10M 107/50* | (2006.01) |
| *B05B 12/08* | (2006.01) |
| *B05B 17/06* | (2006.01) |
| *B05D 1/02* | (2006.01) |
| *B05D 3/04* | (2006.01) |
| *C10N 40/00* | (2006.01) |
| *C10N 30/16* | (2006.01) |
| *C10N 50/08* | (2006.01) |
| *A61M 11/00* | (2006.01) |

(52) U.S. Cl.
CPC ....... *A61L 2420/02* (2013.01); *A61L 2420/04* (2013.01); *A61L 2420/06* (2013.01); *A61M 11/005* (2013.01); *C10M 2229/0445* (2013.01); *C10N 2030/16* (2013.01); *C10N 2040/50* (2020.05); *C10N 2050/08* (2013.01)

(56) References Cited

U.S. PATENT DOCUMENTS

| | | | |
|---|---|---|---|
| 4,940,542 A | 7/1990 | Simizu et al. | |
| 5,046,479 A | 9/1991 | Usui | |
| 5,205,277 A | 4/1993 | Chao-tsung | |
| 5,474,797 A | 12/1995 | Sioshansi et al. | |
| 6,143,370 A | 11/2000 | Panagiotou et al. | |
| 8,315,700 B2 | 11/2012 | Citron | |
| 8,551,555 B2 | 10/2013 | Burghard et al. | |
| 8,790,677 B2 | 7/2014 | Mckay | |
| 8,997,978 B2 | 4/2015 | Stopek | |
| 9,220,294 B2* | 12/2015 | McCullough | A24B 13/00 |
| 9,364,215 B2 | 6/2016 | Stopek | |
| 9,688,459 B2 | 6/2017 | Stanley et al. | |
| 9,848,955 B2 | 12/2017 | Buevich | |
| 9,987,400 B1 | 6/2018 | Chen | |
| 10,314,951 B2 | 6/2019 | Chen | |
| 2002/0022762 A1 | 2/2002 | Beane et al. | |
| 2004/0068294 A1 | 4/2004 | Scalzo | |
| 2004/0220614 A1* | 11/2004 | Scalzo | A61L 17/005 606/228 |
| 2005/0034723 A1* | 2/2005 | Bennett | A61M 11/042 128/203.12 |
| 2005/0181116 A1 | 8/2005 | Worsham | |
| 2005/0188921 A1* | 9/2005 | Malone | C23C 14/28 118/715 |
| 2007/0092494 A1 | 4/2007 | Higgins et al. | |
| 2007/0218197 A1* | 9/2007 | Kurono | H01J 37/32458 427/230 |
| 2007/0254091 A1 | 11/2007 | Fredrickson et al. | |
| 2007/0292305 A1 | 12/2007 | Dempsey | |
| 2009/0099532 A1 | 4/2009 | Cuevas | |
| 2009/0169714 A1 | 7/2009 | Burghard et al. | |
| 2010/0021620 A1* | 1/2010 | Coates | A61L 31/16 427/2.24 |
| 2010/0163435 A1* | 7/2010 | Fischer | A61L 17/005 206/204 |
| 2011/0114744 A1 | 5/2011 | Ricciardi et al. | |
| 2013/0264226 A1 | 10/2013 | Prikril et al. | |
| 2018/0193537 A1 | 7/2018 | Honglei | |
| 2018/0272136 A1 | 9/2018 | Horn | |
| 2019/0125938 A1 | 5/2019 | Chen | |
| 2020/0345885 A1* | 11/2020 | Lewis | A61L 9/122 |

FOREIGN PATENT DOCUMENTS

| | | |
|---|---|---|
| CN | 101909666 A | 12/2010 |
| CN | 102026589 A | 4/2011 |
| CN | 102423266 A | 4/2012 |
| CN | 103083730 A | 5/2013 |
| CN | 203647752 U | 6/2014 |
| CN | 104203125 A | 12/2014 |
| CN | 106730044 A | 5/2017 |
| CN | 107454835 A | 12/2017 |
| EP | 0761243 A1 | 3/1997 |
| EP | 1510558 A1 | 3/2005 |
| EP | 2833799 A1 | 2/2015 |
| EP | 2833799 B1 | 8/2017 |
| WO | 1993/07924 A1 | 4/1993 |
| WO | 2004032704 A2 | 4/2004 |
| WO | 2004037443 A1 | 5/2004 |
| WO | 2009046093 A2 | 4/2009 |
| WO | 2017218832 A1 | 12/2017 |

OTHER PUBLICATIONS

International Search Report dated Feb. 27, 2020 for Application No. PCT/IB2019/060231.

International Search Report dated Feb. 27, 2020 for Application No. PCT/IB2019/060232.

\* cited by examiner

OPERATING ROOM COATING APPLICATOR AND METHOD

CROSS-REFERENCE TO RELATED APPLICATIONS

This application claims the benefit of U.S. Provisional Application No. 62/773,102 filed Nov. 29, 2018, the contents of which are incorporated herein by reference in its entirety for all purposes.

This application is related to U.S. Non-Provisional application Ser. No. 16/697227, and to U.S. Non-Provisional application Ser. No. 16/697228, being filed concurrently herewith and having a common assignee.

FIELD

The present disclosure relates generally to apparatus and method for coating objects with a therapeutic agent, and more particularly, apparatus and methods suitable for use in an operating room to coat surgical instruments or surgical implants with a therapeutic agent in the course of conducting surgery, with minimal interruption and delay.
Environment Each year, about twenty-seven million surgical procedures are performed in the United States. Post-operative or surgical site infections ("SSIs") occur in approximately two to three percent of all cases. This rate corresponds with the occurrence of more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated therein have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-trichloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

US Published Patent Application 2004/0220614 to Scalzo, et. al., incorporated herein by reference in its entirety, describes an antimicrobial suture assembly comprising a containment compartment comprising one or more surfaces having an antimicrobial agent disposed thereon, said antimicrobial agent being selected from the group consisting of halogenated hydroxyl ethers, acyloxydiphenyl ethers, and combinations thereof, in an amount sufficient to substantially inhibit bacterial colonization on said containment compartment; and a suture positioned within the containment compartment, the suture comprising one or more surfaces having an antimicrobial agent disposed thereon, said antimicrobial agent being selected from the group consisting of halogenated hydroxyl ethers, acyloxydiphenyl ethers, and combinations thereof, and at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

SUMMARY

An aspect of the present disclosure provides a coating apparatus for applying a coating of a therapeutic agent, comprising an openable and sealable device compartment; a therapeutic agent positioned in communication with the device compartment; a thermal source for vaporizing the therapeutic agent; and a vacuum source in fluid communication with the device compartment.

In one form, the device compartment has rigid walls, and can be connected to a base, the base incorporating the vacuum source.

In another form, the device compartment is removably and sealably coupled to the base, with electrical and vacuum connections extending between the base and the device compartment.

Advantageously, the therapeutic agent is entrained in a carrier, such as wherein the therapeutic agent is triclosan and the carrier is a silicone sheet or pad or film, or a sheet or pad or film made of an absorbable polymer, for example a lactide glycolide copolymer.

In yet another form, the carrier is positioned adjacent the thermal source.

Alternatively, the device compartment has flexible sides, such that the device compartment is openable and sealable on a first end, and the vacuum source is fluidly connected to a second, sealed end thereof.

In this form, the thermal source can be an electrical resistance heater in the form of a serpentine, electrically resistive foil, disposed in the device compartment.

Advantageously, the coating apparatus can further comprise a first spacer mesh positioned inside the device compartment above the thermal element, and a second spacer mesh positioned between the sides of the device compartment and the thermal element, to provide thermal insulation between the sides of the device compartment and the thermal element.

Also in this form, the therapeutic agent can be coated onto the first spacer mesh, or onto the thermal element, or even loaded onto or into a carrier which is disposed adjacent the thermal element.

In yet another form, the vacuum source and a power source are incorporated in a base, which is separate from the device compartment.

In this form, the vacuum source in the base can be fluidly connected to the device compartment via a flexible hose and the power source can be electrically connected to the thermal source via wire leads configured to carry vacuum and/or electric power leads to the heater in the bag.

Also presented herein is a method for coating an object with a therapeutic agent, comprising placing an object to be coated in an openable and sealable device compartment; sealing the device compartment; applying a vacuum from a vacuum source to the device compartment; vaporizing a therapeutic agent to fill the device compartment and coat the object to be coated with the therapeutic agent; and removing the coated object from the device compartment.

In this form, the vacuum source can be in fluid communication with the device compartment and the vaporizing step is conducted with a thermal source.

In one form, the device compartment has rigid walls and is connected to a base, the base incorporating the vacuum source.

Advantageously, the device compartment is removably and sealably coupled to the base, with electrical and vacuum connections extending between the base and the device compartment.

In this form, the therapeutic agent can be entrained in a carrier, such as wherein the therapeutic agent is triclosan and the carrier is a silicone sheet or pad or film, or a sheet or pad or film made of an absorbable polymer. The absorbable polymer can be a lactide glycolide copolymer.

In this form, the carrier is positioned adjacent the thermal source.

In yet another form, the device compartment has flexible sides and the thermal source comprises resistance heating traces positioned within the flexible sides, and thermally insulated from the flexible sides.

Advantageously, the device compartment is openable and sealable on a first end, and the vacuum source is fluidly connected to a second, sealed end thereof.

In this form, the vacuum source and a power source are incorporated in a base, which is separate from the device compartment.

In another form, the vacuum source in the base can be fluidly connected to the device compartment via a flexible hose and the power source can be electrically connected to the thermal source via wire leads.

In yet another form, the method can comprise promoting deposition of the vaporized therapeutic agent upon the object by establishing a thermal gradient between the object and the vaporized therapeutic agent, such that the object is about 50° C. to about 150° C. cooler than the vaporized therapeutic agent, and contacting the object with the vaporized therapeutic agent.

In this form, the contacting is continued for a time period in the range of approximately 1 to approximately 15 minutes, and wherein during the time period of contacting, the temperature of the object increases by less than 15° C.

Additionally presented herein is a method of depositing a therapeutic agent on an implantable medical device comprising promoting deposition of a vaporized therapeutic agent upon the medical device by establishing a thermal gradient between the medical device and the vaporized therapeutic agent, and contacting the object with the vaporized therapeutic agent.

In one form, the medical device can be about 50° C. to about 150° C. cooler than the vaporized therapeutic agent.

In another form, the method can further comprise opening a device compartment, placing the medical device in the device compartment, and closing the device compartment; evacuating the closed device compartment; communicating the vaporized therapeutic agent to the closed device compartment; and opening the device compartment and removing the medical device.

Additionally, the method can further comprise contacting the medical device with the vaporized therapeutic agent while the vaporized therapeutic agent is in a heated condition. During the contacting, the temperature of the medical device increases by less than 15° C.

BRIEF DESCRIPTION OF THE DRAWINGS

The embodiments shown in the figures of the accompanying drawing and subsequently described herein are presented by way of example, and not by way of limitation. In the figures, like reference numerals refer to similar elements; and wherein:

FIGS. 4A and 4B are perspective views of an operating room coating applicator constructed in accordance with still another embodiment of the present disclosure, wherein

FIGS. 7A-H are perspective views of an example embodiment of a method of coating an object using the operating coating applicator shown in FIGS. 4A and 4B, wherein:

DETAILED DESCRIPTION

The medical and surgical devices referenced herein may include surgical instruments and implantable medical devices, wherein the latter may include but are not limited to orthopedic implants for trauma or joint reconstruction, breast implants, sternum closure devices, pacemakers, mono and multifilament sutures, surgical meshes such as hernia repair mesh, hernia plugs, brachy seed spacers, suture clips, suture anchors, adhesion prevention meshes and films, and suture knot clips. Implantable medical devices may be made of absorbable or non-absorbable polymers, or from suitable metals such as stainless steel, titanium and the like.

An absorbable polymer, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Examples of absorbable medical devices may also include mono- and multi-filament sutures. The multi-filament suture may include sutures wherein a plurality of filaments may be formed into a braided structure.

Examples of non-absorbable medical devices may include orthopedic implants for trauma or joint reconstruction, breast implants, sternum closure devices, pacemakers, mono and multifilament sutures, surgical meshes such as hernia repair mesh, hernia plugs and brachy seed spacers, which may be polymeric or nonpolymeric. Non-absorbable polymers include polyolefins, polyamides, polyesters, and polycarbonates and the like.

Suitable antimicrobial agents for the present process may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, or any material having antimicrobial activity which is sublimatable or vaporizable at temperatures up to about 300° C. without degrading.

One particularly preferred antimicrobial agent may be 2,4,4'-trichloro-2'-hydroxydiphenyl ether, commonly referred to as triclosan (manufactured by Ciba Geigy under the trade name Irgasan DP300 or Irgacare MP). Triclosan is a broad-spectrum antimicrobial agent that has been used in a variety of products, and is effective against a number of organisms commonly associated with SSIs. Such microorganisms include, but are not limited to, genus *Staphylococcus*, *Staphylococcus epidermidis*, *Staphylococcus aureus*, methicillin-resistant *Staphylococcus epidermidis*, methicillin-resistant *Staphylococcus aureus*, and combinations thereof.

During the manufacturing process medical devices may be coated with a composition comprising an antimicrobial agent. The coating may be applied to the device by, for example, dip coating, spray coating, suspended drop coating, or any other coating means. However, such techniques for establishing coatings on packaged surgical devices (implants and/or instruments) during or after their manufacture may present problems. For example, depending on the chemistry and other factors, some coatings may have a tendency to migrate over time from the coated device to its packaging, thereby reducing the amount of coating on the device itself. Again depending on its chemistry and other factors, some coatings may degrade over time and therefore have a limited shelf-life. Robust sterilization processes that can compromise the integrity of the antimicrobial agent, such as gamma irradiation, e-beam irradiation, heat or steam, are often used in primary sterilization processes. Lastly, a coated, packaged device is subject to handling, which may inadvertently mechanically degrade some coatings. Furthermore, these techniques may have rather extended cycle times and may often require rather large machines to apply the coating, which are not conducive for operation in the limited space of an operating room, where time and space are limited.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. One of the most efficacious antimicrobial agents against *Staphylococcus* is 2,4,4'-trichloro-2'-hydroxydiphenyl ether (triclosan). This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the anti-microbial agent diffuses through the medium, and as long as the concentration of the antimicrobial agent is above the MIC, none of the susceptible organism will grow on or around the disk for some distance. This distance is called a zone of inhibition. Assuming the anti-microbial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Advantageously, the effective concentration of triclosan on the surface of a medical device such as a coated suture may be greater than about 0.01 ppm (wt./wt. coating) or between about 30 ppm to 5,000 ppm (wt./wt. suture). The concentration of triclosan on the surface of package or containment compartment may be between about 5 ppm to 5,000 ppm (wt./wt. package or compartment). For other particular applications, however, higher amounts of antimicrobial agent may be useful and should be considered well within the scope of the present disclosure.

Figure 1:
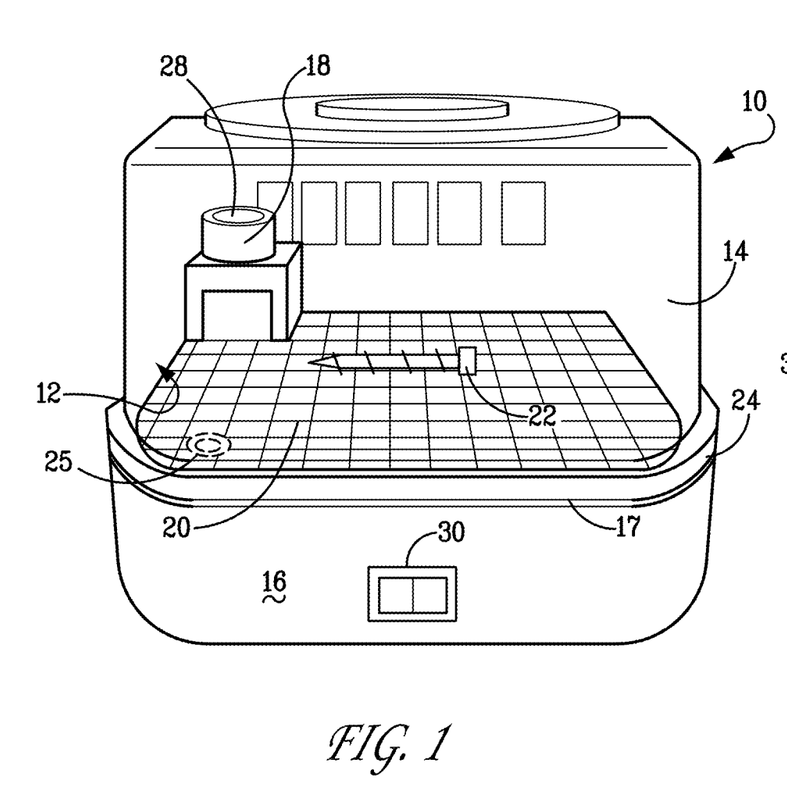
FIG. 1 is a perspective view of an operating room coating applicator constructed in accordance with an embodiment of the present disclosure.

Referring now to FIG. 1 in accordance with an example embodiment, the present disclosure provides an operating room coating applicator 10 comprising a device compartment 12 which may be defined at least in part by the space enclosed when a vacuum lid 14 is engaged in a superposing relation with a base unit ("base") 16. In this and various other embodiments, a thermal source 18 may be supported from the base 16 such that the output from the thermal source 18 is communicated to the device compartment 12. Upon operation of the thermal source 18, a selected therapeutic agent, such as triclosan, may be heated to produce a vapor of the therapeutic agent, which can be loaded onto/into a carrier sheet, pad, cartridge or film 28. When heated, significant vaporization occurs, and the therapeutic agent fills the confines of the device compartment 12.

The base 16 may also house a device supporting platform 20, such as a grate or screen, in a region of the device compartment 12 for receiving an object to be coated 22. In various embodiments, the object 22 may comprise one or more surgical implants and/or surgical instruments and/or other articles useful in conduct of a medical operation. In one embodiment, the device supporting platform 20 is in the form of a lattice grid-work which facilitates circulation of vapor above, below and through the platform 20, and promotes exposure of the surfaces of the object to be coated 22 to the vaporized therapeutic agent produced in the device compartment 12 in the presence of the device 22. The vacuum lid 14 may be readily raised and lowered with respect to the base 16 so as to facilitate placement of the object to be coated 22 on the device supporting platform 20. A resilient O-ring 24 may be provided between edge portions 17 of the vacuum lid 14 and opposing portions of the base to effect a seal between the vacuum lid 14 and the base unit 16. It is envisioned that other suitable arrangements for effecting a seal between the lid 14 and the base 16 might be employed in lieu of or in conjunction with the O-ring seal 24.

In this embodiment, the base unit 16 may house and provide support for a source of vacuum, which vacuum may be communicated to the device compartment 12 through a vacuum port 25 (depicted in dashed lines in FIG. 1 because it is disposed beneath the platform 20 in this illustration). Upon communication of vacuum to the device compartment 12 through the vacuum port 25, vaporization of the therapeutic agent is enhanced by the reduced pressure within the device compartment 12. Accordingly, the temperature necessary to vaporize the therapeutic agent can be reduced. The enhanced vaporization of the therapeutic agent helps to distribute the agent consistently throughout the device compartment 12, and evenly onto the surfaces of the object to be coated 22.

Upon completion of an application cycle, the coated surgical object 22 is removed from the confines of the device compartment 12 in a condition acceptable for immediate use in a surgical procedure being conducted within the sterile field of an operating room or the like. In various embodiments, the coating of the therapeutic agent upon the surgical object 22 may or may not be microscopically uniform. The coating may be in the form of discrete microscopic islands dispersed across the surfaces of the implant or and may have a thickness in the range of approximately 0.05 to 5 micrometer.

In this embodiment and others, the thermal source 18 can be a heating cartridge, a film heater, a silicone heater or a wire based heater, configured to heat a carrier sheet, pad, cartridge or film 28 containing the therapeutic agent to a temperature high enough to cause sublimation or vaporization of the therapeutic agent. The location of the source 18 is not critical, so long as it fluidly communicates with the interior of the device compartment 12 and is close enough to the carrier to cause the therapeutic agent to sublimate or otherwise vaporize. For example, the carrier 28 can be a sheet, pad or film of silicone polymer which is impregnated with triclosan, and wherein the carrier 28 is disposed below the device supporting platform 20. In this embodiment, thermal source 18 would be located beneath the carrier 28. In other embodiments, the thermal source 18 and carrier 28 could be located in a sealed compartment within base 16, having fluid communication with device compartment 12 through a duct or via.

In various embodiments, the base 16 may be provided with a selector switch 30 for switching from one program of operation to another (such as amongst programs which provide differing drying cycles or soak times or the like) and/or for switching from one mode of operation to another and/or simply to turn on and off the operating room coating applicator 10.

Figure 2:
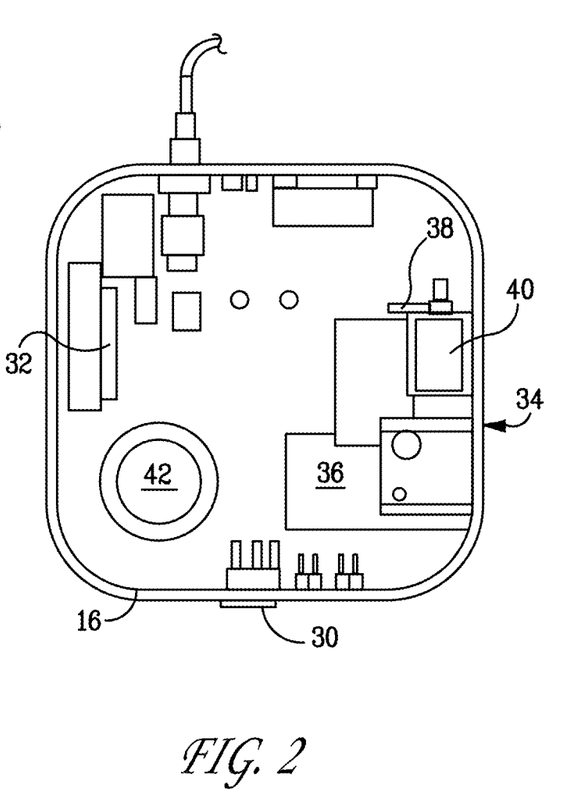
FIG. 2 is a bottom planar view of a base portion of the operating room coating applicator shown in FIG. 1, with its bottom cover plate removed, in accordance with an embodiment of the present disclosure.
Figure 10:
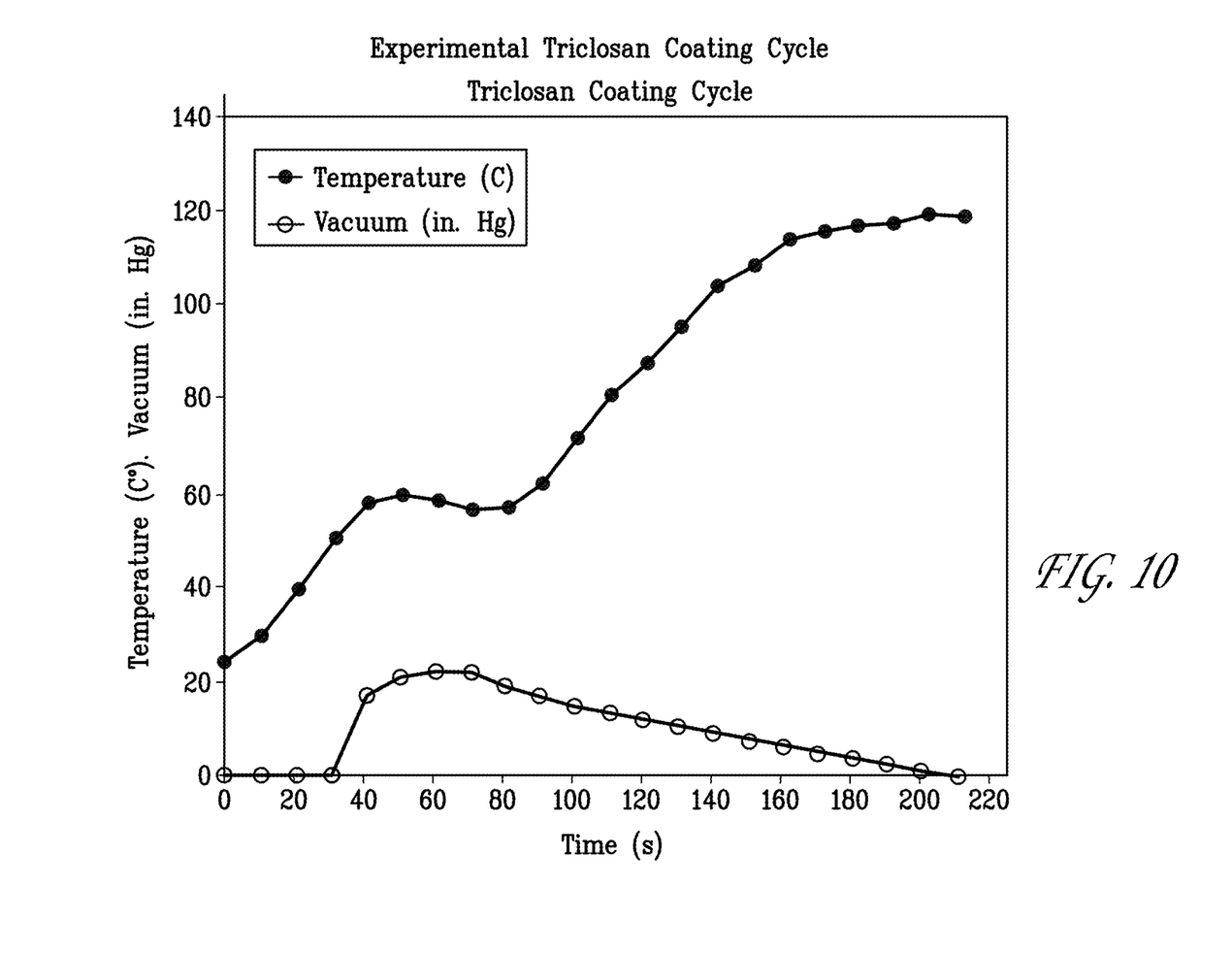
FIG. 10 is a graphical representation of a coating cycle executable by various embodiments of the operating room coating applicator disclosed herein.
Figure 11:
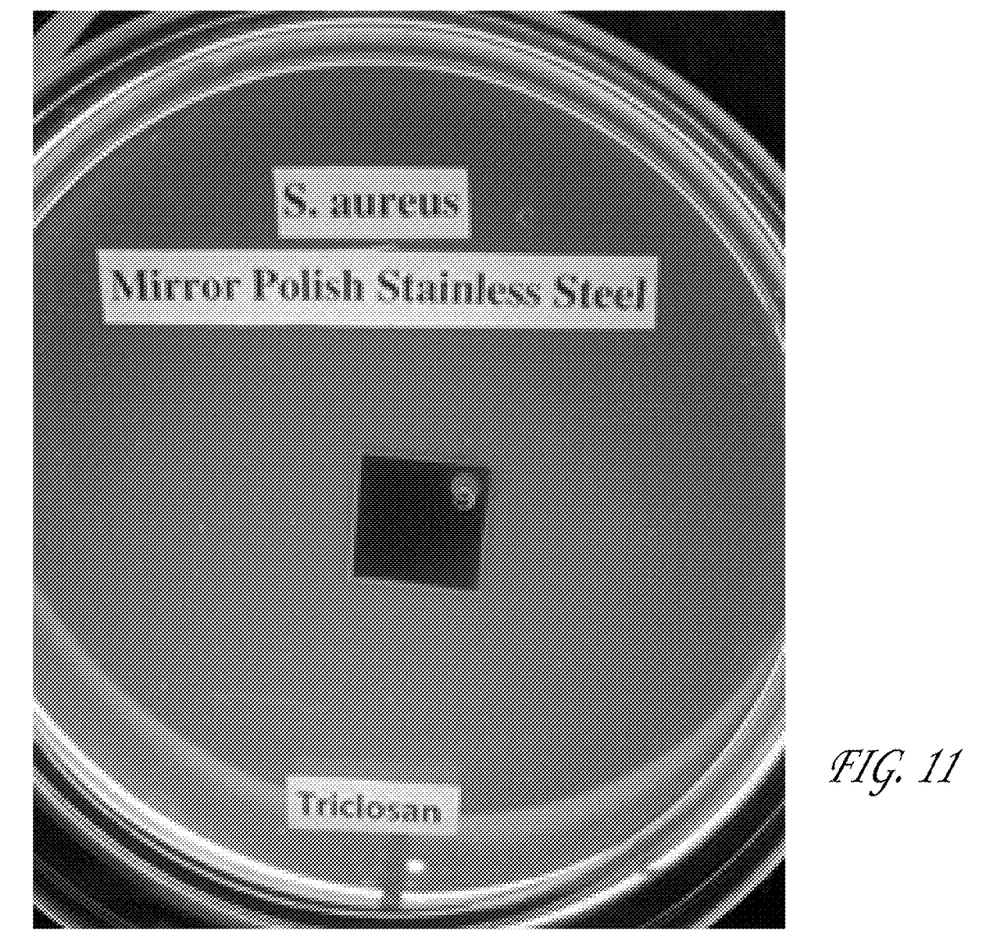
FIG. 11 is a photograph of a zone of inhibition test for triclosan, described in the Example.

Referring now also to FIG. 2, in this embodiment and various others, the base unit 16 may internally house and provide support for a controller 32 which may be in the form of a micro-processor or other suitable electronic arrangement for controlling the timing of a coating cycle, the communication of vacuum with the device compartment 12, operation of the vaporizer 18 and in some other embodiments, the application of heat within the device compartment 12. In the present embodiment and various others, the controller 32 may be configured to execute a coating cycle such as the example coating cycle described with reference to FIG. 10 herein. Upon receipt of a signal to initiate the coating cycle, the controller 32 may turn on and provide electrical power to the thermal source 18 for a prescribed period of time or until a detected level of therapeutic agent has been vaporized from carrier 28. It is envisioned that other detectable factors may be communicated to the controller 32 for purposes of managing the time period for operation of the thermal source 18. The controller 32 may also be configured to draw vacuum from the device compartment 12 for a prescribed period of time and/or upon achievement of a particular prescribed condition within the device compartment 12 and/or according to a program of repeated applications of vacuum, each with a common cycle time and or differing cycle times.

The base unit 16 may further provide support for a vacuum system 34 for communicating a source of vacuum to the device compartment 12, which may comprise a vacuum pump 36 and a conduit 38 for communicating the drawing action of the vacuum pump 36 to the device compartment 12. The vacuum system 34 may further comprise one or more solenoid valves 40 or other suitable valve to open and close the conduit 38 under the direction of the controller 32. During an evacuation of the device compartment 12, the air and other constituents (excess vaporized therapeutic agent) that are withdrawn from the device compartment 12 may be directed through a vapor trap 42, whereby the vaporized therapeutic agent may be collected. Operation of the various components of the vacuum system 34 may be controlled by the controller 32 to repetitively execute a prescribed operational cycle. It is to be understood that during such operation, the drawing action of the vacuum pump 36 may evacuate the device compartment 12 so that upon opening of the device compartment 12 after execution of the cycle, little or no residual therapeutic agent is allowed to escape from the device compartment 12 into the surrounding environment.

In various embodiments, the controller 32 may be configured to operate thermal source 18 for a prescribed time or portion of an application cycle, such as for the first 30 seconds of a 220 second cycle. In some embodiments, the controller 32 may be configured to turn on the vacuum pump 36 upon conclusion of the application cycle. Of course, it is to be understood that the layout and sequence of an application cycle may vary depending on the nature of the object to be coated 22, the therapeutic agent to be applied, the efficiency of the vacuum pump 36 and/or efficiency of the thermal source 18, among other factors.

Figure 3A:
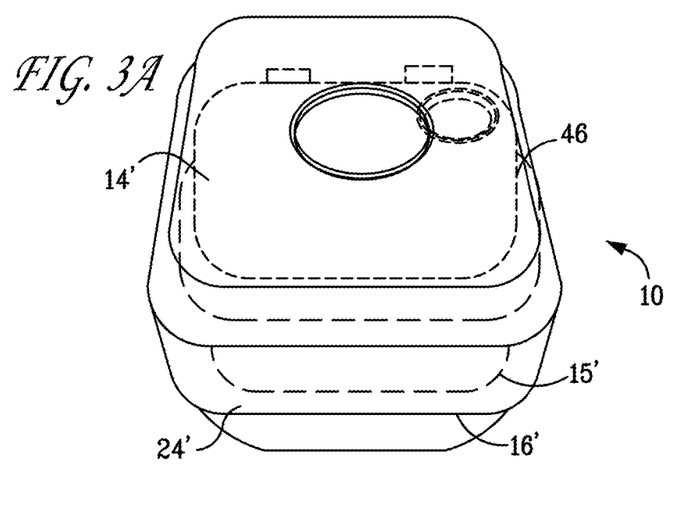
FIG. 3A is a perspective view of an operating room coating applicator constructed in accordance with another embodiment of the present disclosure.
Figure 3B:
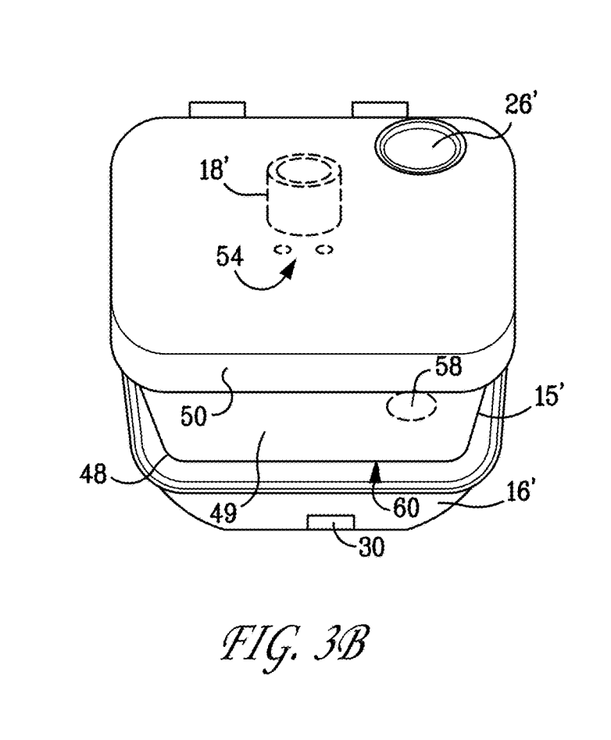
FIG. 3B is a perspective view of the operating room coating applicator shown in FIG. 3A, but with its vacuum lid opened.

Referring now to FIGS. 3A and 3B, in an example of another embodiment, an operating room coating applicator 10 may comprise an openable box-like device compartment 15', which may be configured to fit and lie within a space 46 enclosed by a removable, outer vacuum lid 14' and a base unit 16'. In this embodiment, the device compartment 15' may comprise a lower box body 48 to which is hinged a box body top 50. In various other embodiments, the box body top 50 may be wholly removable from the box body 48 and/or threadably connected with the box body 48. As such, the device compartment 15' may be moved about independently of the base 16' such that the base 16' may be located outside a sterile zone of an operating room and the device compartment 15' may be separately utilized within the sterile zone.

The device compartment 15' may be provided with a vent 26' so as to allow equalization of pressure within the device compartment 15' and the space 46 defined between the vacuum lid 14' and the base 16'. In some embodiments, as the device compartment 15' is evacuated, the space 46 will also be evacuated via the vent 26'. The vent 26' may be constructed of a Tyvek® material and functions to allow pressure within the device compartment 15' to be equalized to the space 46 outside the device compartment 15' and under the vacuum lid 14'. With the use of Tyvek® material or other suitable material of comparable functionality, the vaporized therapeutic agent may be substantially, if not entirely prevented from entering the space 46 outside the device compartment 15' and instead, may remain within the device compartment 15' until it is evacuated by an operation of the vacuum system 34.

In the present embodiment, the walls 49, 51 of the box body 48 and the lid of the box body 50, respectively, may be sufficiently rigid to withstand handling. However, because of the capacity of the vent 26 to equalize pressure on opposite sides of the walls 49, 51, the walls 49, 51 need not withstand the forces that would otherwise be induced by an operation of the vacuum system 34. Accordingly, the walls 49, 51 may be constructed from a thin plastic or other suitable material so as to minimize material waste upon their disposal.

In this and various other embodiments, the operative portion of the thermal source 18' may be wholly disposed within the device compartment 15'.

Figure 3C:
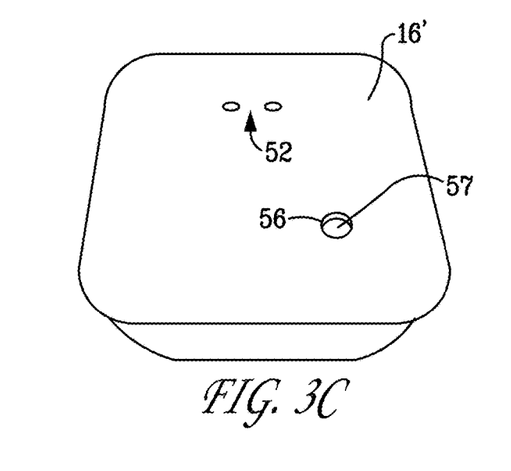
FIG. 3C is a perspective view of the base unit of the operating room coating applicator shown in FIG. 3A, wherein both the vacuum lid and the device compartment box have been removed from the base unit.

Referring now also to FIG. 3C, the base unit 16' may be constructed in accordance with the teachings above in reference to the base 16 that is shown in FIGS. 1 and 2, except that the operative portion of the thermal source 18' may be located in the device compartment 12' instead of the base 16', in which case the base 16' may be provided with a first (electrical) connection 52 for communicating electrical power to the thermal source 18' and to any other electrical device(s) disposed within in the device compartment 12'. Likewise, the device compartment 15' may be provided with a complementary first receiver 54 (FIG. 3B), which electrically connects with the electric contacts of the first electrical connection 52 of the base 16'. In some embodiments, the first electrical connection 52 and/or the receiver 54 may include pins (which may be spring-loaded) or other suitable, releasable, electrical connectors.

The base unit 16' may also be provided with a second (vacuum) connection 56, which may comprise a vacuum port 57 configured to sealingly engage a corresponding vacuum port 58 located at an underside portion 60 of the device compartment 15'. Vacuum port 57 may be provided with O-rings or other suitable seal to establish a vacuum seal at the vacuum connection 56, whereby the vacuum pump 36 of the base 16' may be communicated with the interior of the device compartment 15'.

In some embodiments, the device compartment 15' may be disposable; and both the device compartment 15' and the base 16' may be provided with magnetic pieces that are mutually disposed to assure proper alignment of the electrical contacts 52 and 54 when the device compartment 15' and the base 16' are brought together.

Any of the above described embodiments and variations thereof may be utilized to coat an object 22 with a therapeutic agent where the agent which may be suitable for use with the thermal source and exhibit a relatively high vapor pressure at a temperature below the point at which thermal degradation of the agent can occur. The steps to coat the object with this type of therapeutic agent include:

opening the device compartment 15;
placing an object to be coated 22 upon the device support platform 20;
closing the respective lid (14, 50) of the device compartment 15;
sealing the vacuum lid 14 to the base 16;
drawing a vacuum inside the device compartment 15 for approximately 2 to 3 minutes to evacuate the interior of the device compartment 15, and activating the thermal source 18 to vaporize the therapeutic agent;
releasing the vacuum;
removing the vacuum lid from the base 16;
opening the device compartment 15; and removing the coated object.

In this form it should be understood that the therapeutic agent is pre-deposited onto or into a carrier 28, which is positioned adjacent to the thermal source 18 within the device compartment.

Figure 4A:
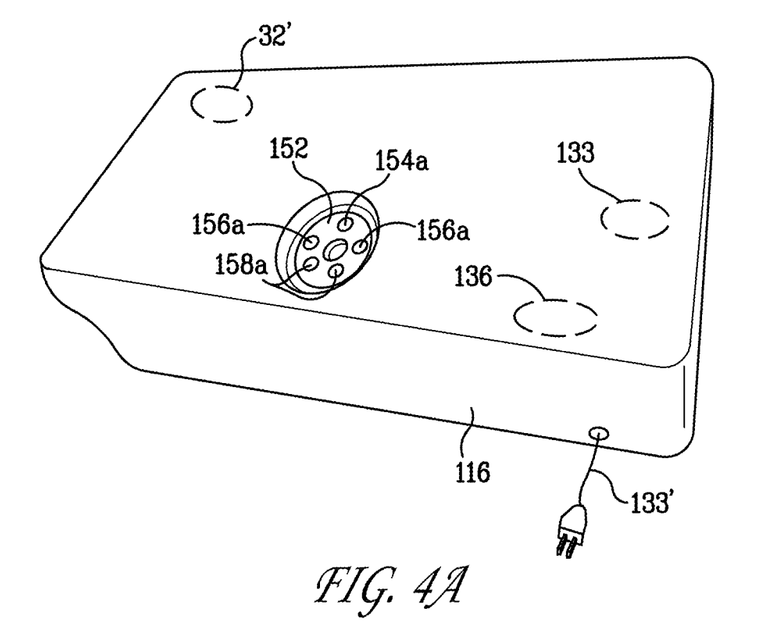
FIG. 4A is a perspective view of an accessory unit of the present embodiment and FIG. 4B is a perspective view of a device compartment bag of the present embodiment coupled with the accessory unit shown in FIG. 4A.
Figure 4B:
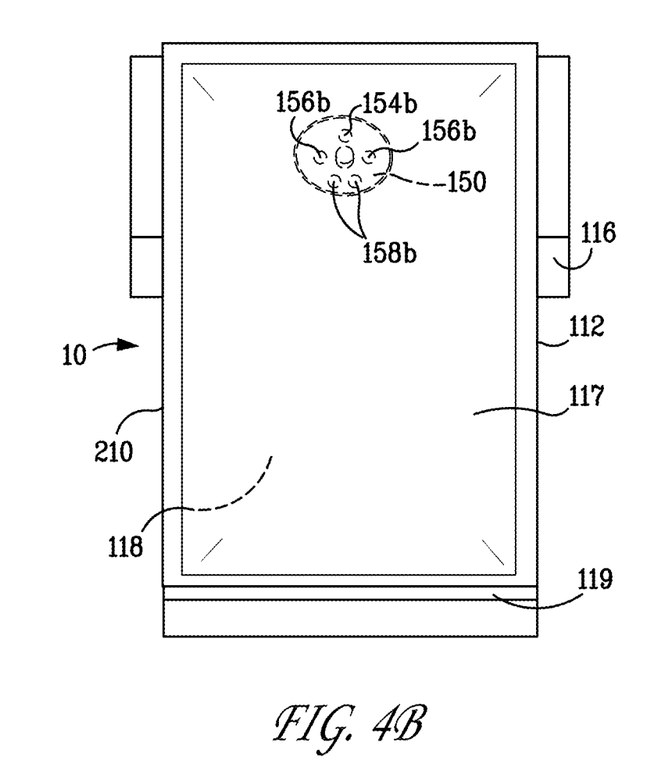
Figure 5:
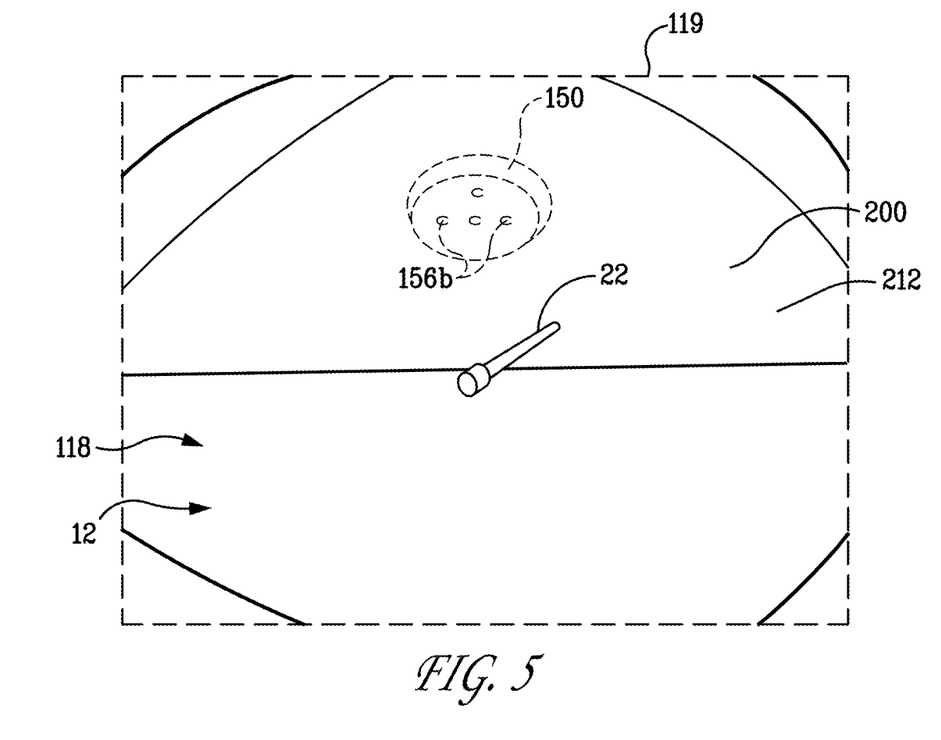
FIG. 5 is a top view of the device compartment bag shown in FIG. 4B, with the bag having been opened, in accordance with an embodiment of the present disclosure.

Referring now to FIGS. 4A, 4B and 5, an example of an operating room coating applicator 10 constructed in accordance with another embodiment of the present disclosure comprises a device compartment bag 112 and an accessory base unit 116 ("accessory"), the latter having many of the functionalities of the base units 16, 16' described in reference to the previously disclosed embodiments. In contrast to the rigid (or semi-rigid walls) of the device compartments 15, 15' of the previous embodiments, the walls 117 of the device compartment bag 112 may be flexible and may be opened along a ribbed closure 119 to accommodate placement of the object to be coated 22 within the confines (interior) 118 of the device compartment bag 112. The interior 118 of the device compartment bag 112 functions as a device compartment. The interior 118 the device compartment bag 112 may also accommodate certain components of the applicator 10 such as the thermal source (not shown). The device compartment bag 112 may also be provided with an adapter ("connector") 150 which is configured to releasably connect with a second corresponding adapter ("connector") 152 which may be provided upon the accessory 116. Engagement of the adapter 150 with the adapter 152 may be achieved with a sliding fit therebetween or a claw and detent engagement or other suitable releasable arrangement. It is to be understood that in FIG. 4B, the adapter 150 of the device compartment bag 112 is hidden from view and therefore represented by dashed lines.

The adapters 150, 152 may be provided with corresponding vacuum ports 154a, 154b for establishing communication between a source of vacuum 136 of the accessory 116 and the interior 118 of device compartment bag 112. The adapters 150, 152 may be provided with corresponding pairs of electrical connectors 156a, 156b, which may comprise spring-loaded, metallic pins or other suitable, releasable, electrical connection devices. Additional electrical connectors may be established on the adapters 150, 152 to connect other devices with the source of power 133 of the accessory 116. In various embodiments, the source of power 133 may comprise a battery or a pack of batteries disposed within the accessory 116 or may instead or in addition comprise an electrical cord 133' for connection with an external electrical wall socket or an external battery or the like.

Alternatively, the adapter 152 of the accessory 116 may include spring-loaded pins at its location 158a which may serve as probes for temperature measurement and/or for pressure measurement and/or for transmitting electrical power to the thermal source. These pins could be extendable through ports established at the corresponding locations 158b of the adapter 150 of the device compartment bag 112.

Figure 6:
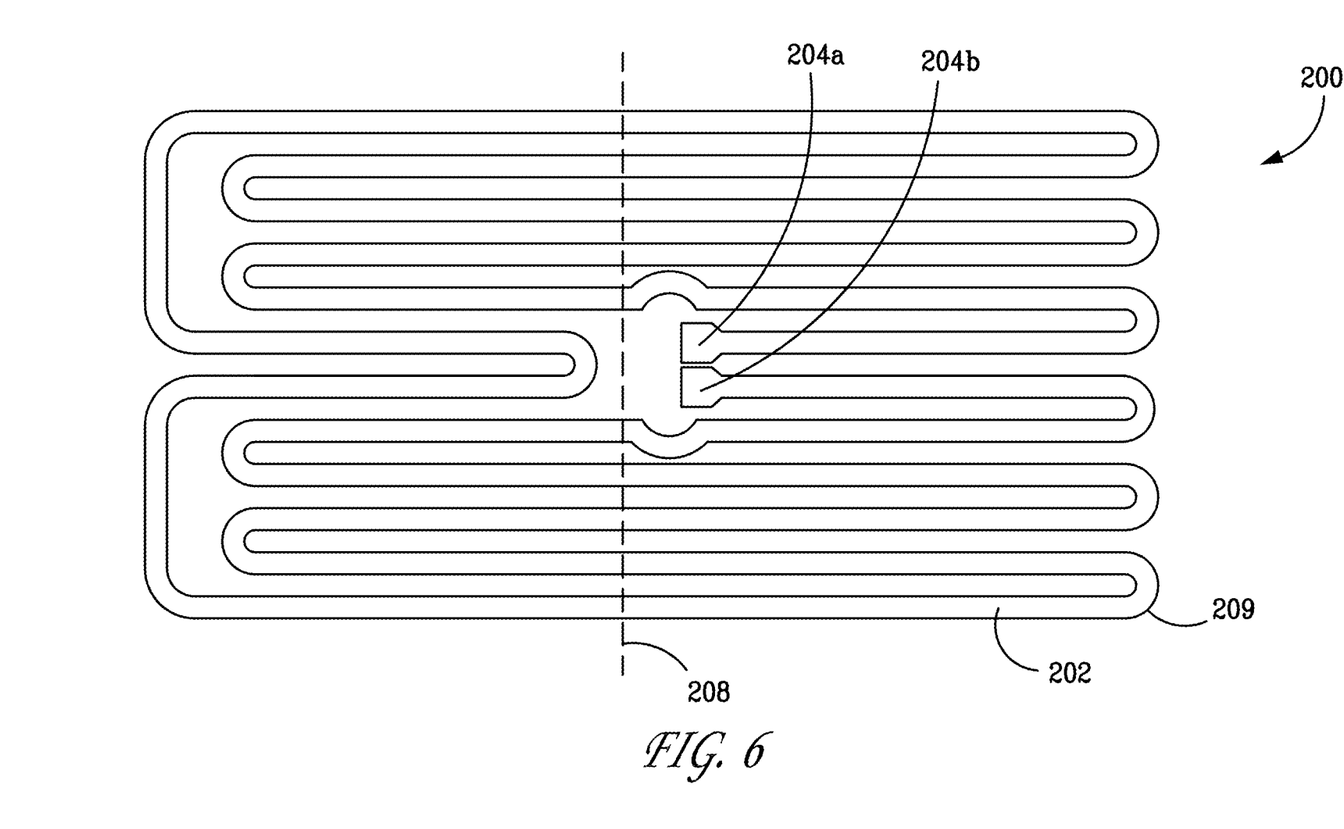
FIG. 6 is a top planar view of a possible pattern of an electrically resistive heater element prior to its being folded into the form of the device compartment bag shown in FIG. 5, with the device component bag having been opened.

Referring now to FIG. 5, electrical contacts 156b make intimate contact with the thermal source 200, in this case a resistive heater comprising a serpentine conductive foil 202, which is a flexible electrical heating element comprised of an aluminum/PET laminate in this example, disposed within the device compartment bag 112. The resistive heater 200 operates under the direction of the controller 32' (FIG. 4A) to serve as a thermal driver to volatilize the therapeutic agent or other agent from a substrate. Referring specifically to FIG. 6, in some embodiments, the resistive heater may be constructed from a serpentine electrically resistive foil 202 insulated from the flexible (outer) wall 117 of the device compartment bag 112, such as where the resistive foil 202 is sandwiched between two spacer layers 212.

In various embodiments, the serpentine conductive foil 202 may be provided with electrical terminals 204a, 204b in the form of tabs to which the pins of 156b (FIG. 5) can be abutted. In constructing the resistive heater 200, the serpentine foil 202 may be sufficiently robust to be free standing or may be first established upon a PET or polyimide substrate 209, and then folded along a central transverse fold line 208. In some embodiments the substrate 209 make might comprise a carrier doped with a therapeutic agent such as triclosan and/or might comprise instead, or in addition a sheet of the material comprising the flexible walls 117 of the device compartment bag 112. In various embodiments, the walls 117 may be constructed from a flexible heat resistant material such as PET or polyimide, and may include a printed layer of conductive material in the aforementioned serpentine array or other pattern. In various other embodiments, a spacer layer 212 may be interposed between the serpentine heater array 200 and the walls 117 of the device compartment bag 112. Such polymeric mesh spacer materials are well-known in the art.

Referring back to FIGS. 4A and 4B, after the aforementioned folding, the device compartment bag 112 may be formed by sealing the outer perimeter 210 along three sides of the folded walls 117 and a resealable ribbed seal 119 may be established across the remaining end portion of the device compartment bag 112. In some embodiments, the adapter 150 of the device compartment bag 112 be located adjacent the ribbed seal 119 and in other embodiments, the adapter 150 may be located in a spaced relation to the resealable ribbed seal 119.

Figure 7A:
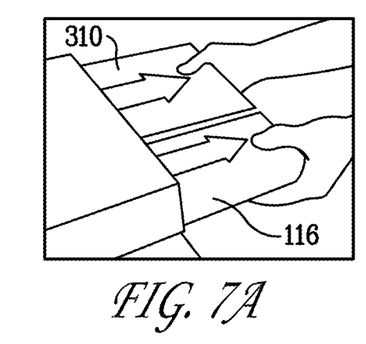
FIG. 7A shows an example of retrieving an accessory unit and a sealed packet containing a device compartment bag at a location outside a sterile zone of an operating room.
Figure 7B:
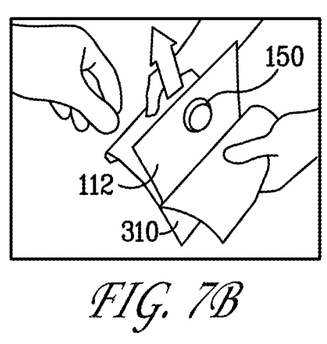
FIG. 7B shows an example of transferring a device compartment bag into the sterile field of an operating room and opening the packet.
Figure 7C:
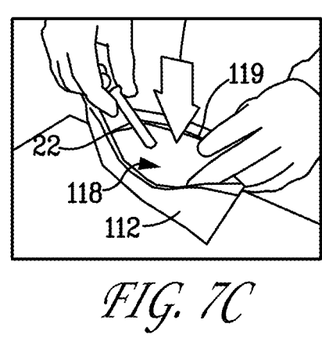
FIG. 7C shows an example of inserting a surgical implant into an opened device compartment bag at a location within the sterile field.
Figure 7D:
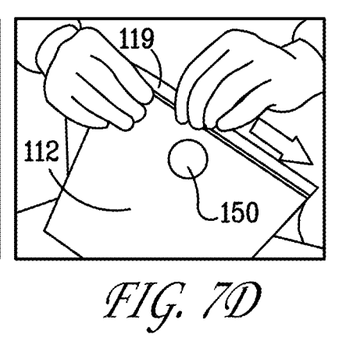
FIG. 7D shows an example of resealing the device compartment bag while at the location within the sterile field.
Figure 7E:
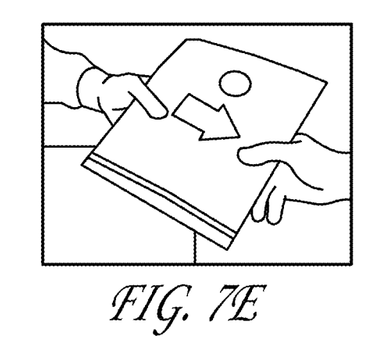
FIG. 7E shows an example of transferring the re-sealed device compartment bag out of the sterile field of an operating room.
Figure 7F:
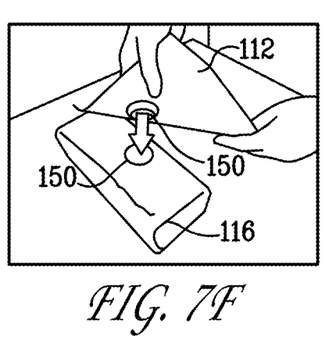
FIG. 7F shows an example of connecting the resealed device compartment bag an accessory unit at a location outside of the sterile field.
Figure 7G:
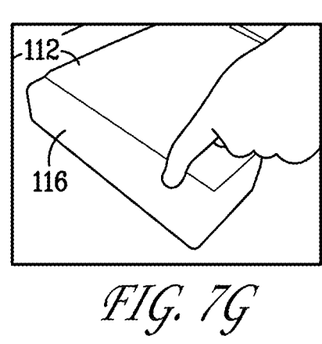
FIG. 7G shows an example of starting the accessory unit to execute a coating application cycle.
Figure 7H:
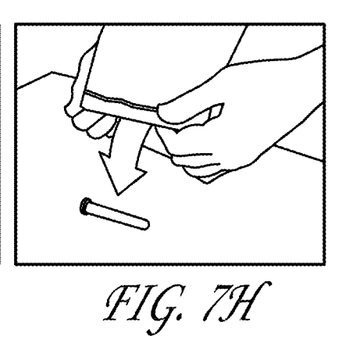
FIG. 7H shows an example of transferring a coated implant into the sterile field of an operating room after completion of the coating application cycle and returning the resealed device compartment bag to within the sterile field.
Figures 8A, 8B:
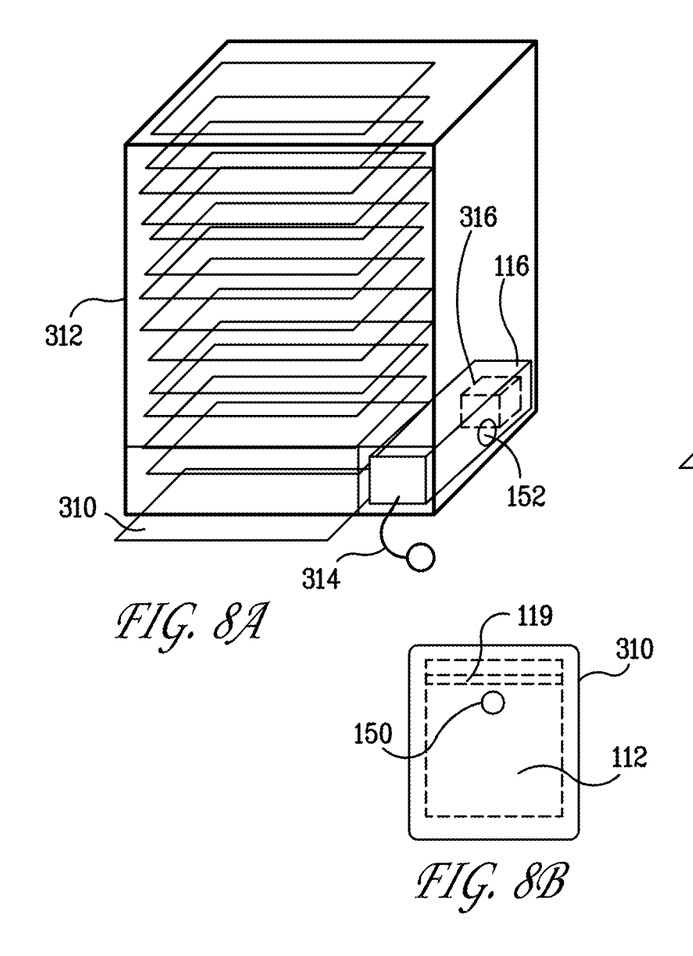
FIG. 8A is a perspective representation of an example of a dispenser configured to dispense a plurality of sealed packets of device compartment and fixedly support an accessory unit thereon, in accordance with still another embodiment of the present disclosure.
FIG. 8B is a planar side view of an example of a sealed packet of an applicator bag of the embodiment shown in FIG. 8A.
Figure 9A:
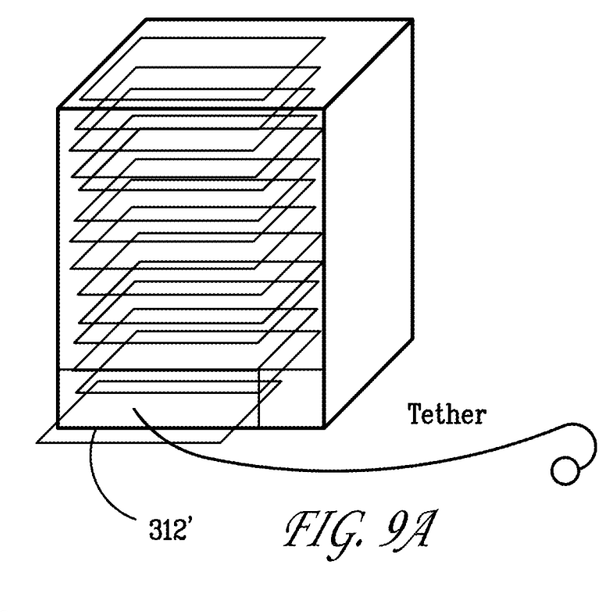
FIG. 9A is a perspective representation of an example of another dispenser filled with sealed packets of applicators, in accordance with yet another embodiment of the present disclosure.
Figure 9B:
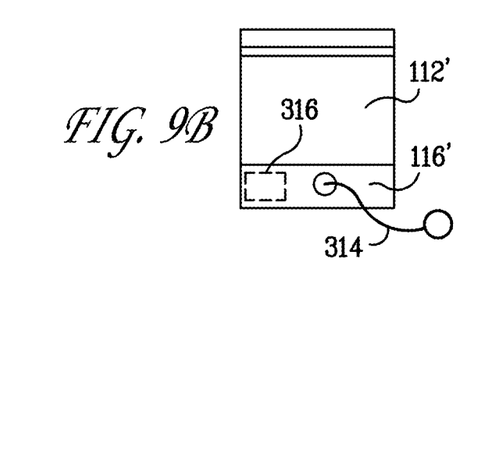
FIG. 9B is a planar side view of an example of an applicator of a sealed packet as shown in FIG. 9A, with the outer primary packaging used to ensure sterility of the device compartment bag contained within having been removed.

Referring again to FIG. 5, the device compartment bag 112 may further comprise a second, inner spacer layer 212 which may be constructed from a layer of polymeric mesh. In various embodiments, the inner spacer layer 212 (a standoff spacer) helps assure that outer surfaces of the object to be coated 22, when placed within the device compartment 12 of a closed device compartment bag 112, are exposed to and contacted by the vaporized therapeutic agent as established by the operation of the thermal source 18, in the form of a carrier pad, sheet, cartridge or film (not shown) placed within the device compartment bag 112. The standoff spacer 212 may provide about 0.5 to 2 mm of spacing between the object to be coated 22 and the serpentine resistive foil 202. In various other embodiments, the standoff spacer layer 212 may be supplemented or replaced with other spacing expedients such as plastic ribbing or the like.

The source of electrical power 133 of the accessory 116 may comprise one or more batteries and/or a plug-in connector for a wall socket 133'.

Referring now to FIGS. 7A-H, for those embodiments comprising a device compartment bag 112 and an accessory unit 116, a method of applying a therapeutic agent to a medical device 22 such as a surgical implant or surgical instrument may be practiced by conducting the following, by way of an example:

- retrieving the packet 310 and an accessory 116 from a dispenser 312 and removing the device compartment bag 112 from its packet 310, wherein the latter may be conducted within the sterile field of an operating room (see FIGS. 7A, B);
- opening the device compartment bag 112 in the sterile field of an operating room and inserting the article to be coated 22 (such as a medical device) into the device compartment bag 112 (see FIG. 7C);

closing and resealing the device compartment bag 112 (which may be undertaken in the sterile field) (see FIG. 7D);

transferring the sealed device compartment bag 112 out of the sterile field to a location of the accessory unit 116, which may be outside the sterile field (see FIG. 7E);

temporarily attaching the adapter 150 of the sealed device compartment bag 112 to the adapter 152 of the accessory unit 116 and activating the latter to execute a coating cycle, which may include the following: (see FIGS. 7F, 7G):

drawing a vacuum and heating the thermal source for a desired time inside the sealed device compartment bag 112 to vaporize the therapeutic agent within the device compartment bag 112 and coat the object 22;

releasing the vacuum;

transferring the coated object 22 within sealed bag 112 to the sterile field of the operating room; and opening the device compartment bag 112 and removing the coated object 22 from the bag 112 within the sterile field (see FIG. 7H).

Referring to FIGS. 8A and 8B, a device compartment bag 112 may be individually packaged in a sterile condition within the confines of an openable, sealed packet ("primary package") 310. Multiple packets 310 may be stacked in a dispenser 312 from which individual packets 310 may be withdrawn. The accessory base unit 116 may be affixed to the dispenser 312 and may be removably attachable to any one of the device compartment bags 112 once a packet 310 is removed from the dispenser 312 and the packet 310 opened. In this embodiment the device compartment bag 112 may be configured for a single use.

The accessory unit 116 may be supported by the same carton/dispenser 312 from which the individual packets 310 are housed. The adapter 152 of the accessory unit 116 may be disposed in a manner that facilitates temporary attachment of the device compartment bag 112 to the accessory unit 116 when pressing adapters 152 and 150 together. Requisite electrical power and vacuum may be communicated to the accessory 116 unit via a connection or tether 314 to an external source of power such as an electric wall socket and an external source of vacuum. In various other embodiments, the accessory unit 116 may include its own batteries 316 to drive devices such as a vacuum pump 36 within the accessory unit 116. A controller 32' (FIG. 4A) may also be located within the accessory 116 or instead remotely communicated through the tether 314. The thermal source 18 may be located within the confines of the device compartment bag 112.

Referring now to FIGS. 9A and 9B in another embodiment, the accessory unit 116' may be integrated with the device compartment bag 112 so as to form a unitary complete unit that may be disposable after a single use. The accessory portion 116' may be solely battery-powered or solely powered by a connection through a tether 314 to an external electric source such as an electric wall socket or both. In various embodiments, the integrated device compartment bag 112' and accessory 116', together with tether 314 may all be packaged within an individual packet 310'. In this and various other embodiments, the vacuum source (pump) 36 may be an external vacuum source 36 which is communicated to the accessory 116' and/or the device compartment bag 112 through the tether 314.

Referring now to FIG. 10, the controller of the base or the accessory may be configured to execute an application cycle which comprises a period in which the thermal source 18, 200 is turned on to vaporize triclosan. As represented in FIG. 10, the ramp up temperature within the device compartment 12, 112 may be increased as vacuum level decreases during the coating cycle. Subsequently to the coating cycle, the temperature and pressure of the device compartment are returned to ambient.

The Cold Finger Effect

Since the implant is in-part thermally insulated from the thermal source 202 by a standoff mesh 212, and by virtue of the fact that the process occurs rapidly and the thermal mass of the implant is large with respect to the thermal mass of heating element, thermal equilibrium between the thermal source and the implant never occurs. Consequently the implant is usually significantly cooler than the thermal source. The temperature difference (or thermal gradient) can be from about 50° C. to about 150° C. for a coating device designed to coat triclosan onto an implant or other medical device. As such, a very significant thermodynamic driving force for condensation of the hot vapor on the relatively cold surface of the implant is present. This helps to drive the condensation of the active agent onto a variety of different surfaces that the active agent would otherwise not preferably absorb onto. In this way the presently disclosed device and method differs significantly from previous processes used to make triclosan impregnated absorbable sutures, such as disclosed in US Published Patent Application 2004/0220614 to Scalzo, et. al.

EXAMPLES

A triclosan coating was applied to a 0.5" polished 316 stainless steel coupon using the device described in FIGS. 1 and 2 according to the cycle described in FIG. 10. The stainless steel coupon was then incubated at 38° C. for 24 hours on an agar plate containing an initial *Staphylococcus aureus* inoculum of $10^5$ bacteria per cubic centimeter of solution. The image shown in FIG. 11 indicates that a protective zone of inhibition of approximately 40 mm was formed throughout the entire 80 mm diameter plate. Notably, the entire plate was protected.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

While the present disclosure is being illustrated and described below by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A coating apparatus for applying a coating of a therapeutic agent, comprising:
    an openable and sealable device compartment;
    a therapeutic agent positioned in communication with the device compartment;
    a thermal source for vaporizing the therapeutic agent; and
    a vacuum source in fluid communication with the device compartment,
    wherein the device compartment is connected to a base, the base incorporating the vacuum source,
    wherein the device compartment is removably and sealably coupled to the base, with electrical and vacuum connections extending between the base and the device compartment,
    wherein the therapeutic agent is entrained in a carrier, and
    wherein the therapeutic agent is triclosan and the carrier is a silicone sheet or pad or film, or a sheet or pad or film made of an absorbable polymer.

2. The coating apparatus of claim 1, wherein the device compartment has rigid walls.

3. The coating apparatus of claim 1, wherein the absorbable polymer is lactide glycolide copolymer.

4. The coating apparatus of claim 1, wherein the carrier is positioned adjacent the thermal source.

5. The coating apparatus of claim 1, wherein the therapeutic agent is triclosan.

6. The coating apparatus of claim 1, wherein the device compartment has flexible sides.

7. The coating apparatus of claim 6, wherein the thermal source is an electrical resistance heater in the form of a serpentine electrically resistive foil, disposed in the device compartment.

8. The coating apparatus of claim 7, further comprising a first spacer mesh positioned inside the device compartment above the thermal source, and a second spacer mesh positioned between the sides of the device compartment and the thermal source, to provide thermal insulation between the sides of the device compartment and the thermal source.

9. The coating apparatus of claim 8, wherein the therapeutic agent is coated onto the first spacer mesh.

10. The coating apparatus of claim 8, wherein the therapeutic agent is coated onto the thermal source.

11. The coating apparatus of claim 8, wherein the therapeutic agent is loaded onto or into a carrier which is disposed adjacent the thermal source.

12. The coating apparatus of claim 7, wherein the device compartment is openable and sealable on a first end, and the vacuum source is fluidly connected to a second, sealed end thereof.

13. The coating apparatus of claim 12, wherein the vacuum source and a power source are incorporated in a base, which is separate from the device compartment.

14. The coating apparatus of claim 13, wherein the vacuum source in the base is fluidly connected to the device compartment via a flexible hose and the power source is electrically connected to the thermal source via wire leads configured to carry vacuum and/or electric power leads to the electrical resistance heater in the device compartment.

* * * * *